US012678634B2

(12) United States Patent
Kim et al.

(10) Patent No.: US 12,678,634 B2
(45) Date of Patent: Jul. 14, 2026

(54) SKIN CARE DEVICE USING MULTIPLE COMPOSITE LASER PULSES AND METHOD THEREOF

(71) Applicant: JEISYS MEDICAL INC., Seoul (KR)

(72) Inventors: Seong Jun Kim, Seoul (KR); Kyu Jin Park, Seoul (KR); Chul Yong Ahn, Seoul (KR); Won Ju Yi, Seoul (KR); Dong Hwan Kang, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 240 days.

(21) Appl. No.: 18/414,851

(22) Filed: Jan. 17, 2024

(65) Prior Publication Data

US 2024/0181273 A1 Jun. 6, 2024

Related U.S. Application Data

(63) Continuation of application No. PCT/KR2022/008323, filed on Jun. 13, 2022.

(30) Foreign Application Priority Data

Jul. 19, 2021 (KR) ........................ 10-2021-0093957

(51) Int. Cl.
*A61N 5/067* (2006.01)
*A61N 5/06* (2006.01)

(52) U.S. Cl.
CPC ........... *A61N 5/067* (2021.08); *A61N 5/0616* (2013.01); *A61N 2005/0627* (2013.01); *A61N 2005/0665* (2013.01)

(58) Field of Classification Search
CPC ........ A61N 5/067; A61N 5/0616; A61N 5/06; A61N 2005/0627; A61N 2005/0626;
(Continued)

(56) References Cited

U.S. PATENT DOCUMENTS 5,507,739 A 4/1996 Vassiliadis et al.
5,818,580 A 10/1998 Murnick
(Continued)

FOREIGN PATENT DOCUMENTS

EP 3711819 A1 9/2020
JP S50120797 A 9/1975
(Continued)

OTHER PUBLICATIONS

European Search Report regarding Application No. 22846046.5, Aug. 27, 2024.
(Continued)

*Primary Examiner* — Nathan J Jenness

(57) ABSTRACT

A skin care device using multiple composite laser pulses according to an embodiment of the present disclosure includes: a laser generating unit including an energy portion configured to supply energy, a light emission portion configured to generate light by absorbing the energy supplied from the energy portion, a first mirror and a second mirror configured to form a resonance path in which the light generated from the light emission portion is amplified, a polarizing portion disposed on an optical resonant path between the first mirror and the second mirror and configured to polarize the light, and a first switch and a second switch configured to convert a polarization component of an incident polarized light; and a control unit configured to control the first switch and the second switch so that the laser generating unit operates in a single laser pulse mode or a multiple laser pulse mode.

15 Claims, 7 Drawing Sheets

(58) Field of Classification Search
CPC .......................... A61N 2005/073; A61B 18/20;
A61B 18/203; A61B 18/00; A61B 18/22;
A61B 2018/00702; A61B 2018/00452;
A61B 2018/20553; A61B 2018/205547;
A61B 2018/2283; A61B 2018/2065;
A61B 2018/208; A61B 2017/00168;
A61B 2017/00176; A61B 2017/00769
See application file for complete search history.

(56) References Cited

U.S. PATENT DOCUMENTS

| | | | | |
|---|---|---|---|---|
| 6,078,606 | A | * | 6/2000 | Naiman .................. F41G 3/145 |
| | | | | 372/17 |
| 7,427,289 | B2 | | 9/2008 | Sierra et al. |
| 2006/0161142 | A1 | | 7/2006 | Sierra et al. |
| 2009/0054956 | A1 | | 2/2009 | Sierra et al. |
| 2013/0035676 | A1 | * | 2/2013 | Mitchell ................ A61B 18/22 |
| | | | | 606/16 |
| 2013/0296835 | A1 | | 11/2013 | Sierra et al. |
| 2020/0237438 | A1 | | 7/2020 | Seo |
| 2023/0134604 | A1 | * | 5/2023 | Maeng .............. H01S 3/094076 |
| | | | | 372/17 |

FOREIGN PATENT DOCUMENTS

| | | | |
|---|---|---|---|
| JP | 2013528414 | A | 7/2013 |
| KR | 10-2011-0122478 | A | 11/2011 |
| KR | 10-1252882 | B1 | 4/2013 |
| KR | 10-2013-0125154 | A | 11/2013 |
| KR | 10-1576870 | B1 | 12/2015 |
| KR | 10-1843693 | B1 | 3/2018 |
| KR | 10-2021-0014806 | A | 2/2021 |

OTHER PUBLICATIONS

Japanese Patent Office, Notice of Reasons for Refusal regarding JP Application No. 2024-503777, Dec. 16, 2024.
International Search Report issued in PCT/KR2022/008323; mailed Sep. 27, 2022.
Office Action issued in KR 10-2021-0093957; mailed by the Korean Patent Office on May 22, 2023.
International Preliminary Report on Patentability received for PCT Patent Application No. PCT/KR2022/008323, mailed on Feb. 1, 2024, 11 pages (7 pages of English Translation and 4 pages of Original Document).

* cited by examiner

SKIN CARE DEVICE USING MULTIPLE COMPOSITE LASER PULSES AND METHOD THEREOF

CROSS-REFERENCE TO RELATED APPLICATIONS

The present application is a continuation of International Patent Application No. PCT/KR2022/008323, filed on Jun. 13, 2022, which is based upon and claims the benefit of priority to Korean Patent Application No. 10-2021-0093957 filed on Jul. 19, 2021. The disclosures of the above-listed applications are hereby incorporated by reference herein in their entirety.

BACKGROUND

1. Technical Field

An embodiment of the present disclosure relates to a skin care device and a method thereof, and more particularly, to a skin care device using a multiple composite laser pulse and a method thereof.

2. Description of Related Art

A laser is an acronym of light amplification by stimulated emission of radiation and refers to light amplified by stimulated emission of radiation or a device emitting the light.

Laser light has a very accurate wavelength, as compared to sunlight or light emitted from a general light source, and has a good directivity of a light bundle.

Generally, a laser device includes an active medium, a pumping energy source, and a resonator.

The active medium is a material that emits laser light through an induced emission process after being in an excited state with high energy and, is formed of a luminous body such as atoms, ions, or molecules. The pumping energy source supplies energy to the active medium to raise the luminous body, which has fallen to a ground state while emitting laser light, back to an excited state, so that the luminous body can emit laser light again. The resonator includes reflectors such as two mirrors and does not allow the light generated from the active medium to escape immediately, but rather amplifies the light by emitting new light through the induced emission process.

A laser may be classified as a solid laser, a liquid laser, and a gas laser, depending on the state of the active medium.

For example, the solid laser includes a semiconductor laser, an Nd-YAG laser, a titanium (Ti)-sapphire laser, and an optical fiber laser. The liquid laser includes a pigment laser, and the gas laser includes a helium-neon laser, a carbon dioxide laser, and an excimer laser.

A laser may be classified as an infrared laser, a visible laser, an ultraviolet laser, and an X-ray laser, depending on the wavelength band of light.

For example, the infrared laser includes an infrared optical fiber laser, a carbon dioxide laser, an Nd-YAG laser, a titanium-sapphire laser, and a semiconductor laser emitting infrared light. The visible laser includes a helium-neon laser, and a semiconductor laser emitting red, green, blue, and violet lights, and the ultraviolet laser includes an excimer laser.

A laser may be classified i as a pulse laser and a continuous wave (CW) laser depending on the type of generated light.

For example, the pulse laser generates light in a pulse shape, and the continuous wave laser generates continuous light.

Meanwhile, the pulse laser may generate laser in the shape of a single pulse or multiple pulses.

A laser may be used in various fields such as industrial, medical, and military uses. Particularly, the medical laser may locally focus a predetermined amount of energy and conduct a non-invasive treatment, and accordingly, widely used in surgery, internal medicine, ophthalmology, dermatology, dentistry, and the like.

Furthermore, conventional skin care lasers use a multiple laser pulse to enhance skin care effects through high energy output. Particularly, Patent Publication No. 10-2011-0122478 of the present applicant discloses a laser generating apparatus capable of obtaining more output energy with the same input energy and increasing skin care effects by generating a multiple laser pulse using a cue switch driver for driving a single laser pulse.

However, to obtain various skin care effects, laser pulses of various time widths are required. For example, a laser pulse of several nanoseconds (ns) to tens of ns may be effective for a skin care procedure such as pigmented lesion or tattoo removal, a laser pulse of several microseconds (μs) to hundreds of μs may be effective for skin care such as rejuvenation, such as tightening wrinkle improvement, and two laser pulses of several ns to tens of ns and several μs to hundreds of μs may be used to effectively process the two types of skin care.

For this purpose, one of the conventional skin care devices uses a queue switch driver that drives a laser pulse and a motor that drives a waveplate driven in/out of a resonator to generate a pulse laser of several ns to tens of ns and a pulse laser of several μs to hundreds of μs, thereby enabling skin care by the pulse laser of several μs to hundreds of μs after skin care by the pulse laser of several ns to tens of ns with one device.

However, the conventional skin care device has a problem in that the wave plate is driven by the mechanical operation of the motor, which slows the speed of driving in/out of the resonator, which prevents the repeated generation of pulses of various time widths over a short period of time, and thus cannot simultaneously obtain various skin care effects by multiple laser pulses of different widths.

SUMMARY

A technical problem to be solved by the present disclosure is to provide a skin care device using a multiple composite laser pulse and a method thereof, which may simultaneously obtain various skin care effects by generating multiple laser pulses of various time widths.

Another technical problem to be solved by the present disclosure is to provide a skin care device using a multiple composite laser pulse and a method thereof, which can simultaneously obtain the skin care effect, such as removal of pigmented lesions or tattoos, by a laser pulse of several ns to tens of ns and the skin care effect, such as rejuvenation such as tightening wrinkle improvement, by a laser pulse of several μs to hundreds of μs by repeatedly generating the laser pulse of several ns to tens of ns and the laser pulse of several μs to hundreds of μs.

Still another technical problem to be solved by the present disclosure is to provide a skin care device using a multiple composite laser pulse and a method thereof, which can simultaneously obtain the skin care effect, such as removal of pigmented lesions or tattoos, by a laser pulse of several ns to tens of ns, and the skin t care effect, such as rejuvenation such as tightening wrinkle improvement, by a laser pulse of several μs to hundreds of μs by repeatedly and continuously generating the laser pulse of several ns to tens of ns and the laser pulse of several μs to hundreds of μs at time intervals of about hundreds of μs to hundreds of ms.

Still another technical problem to be solved by the present disclosure is to provide a skin care device using a multiple composite laser pulse and a method thereof, which can implement multi-laser pulses easily and significantly reduce the time interval between multi-laser pulses by providing at least two electrical switches for repeatedly and continuously generating the laser pulse of several ns to tens of ns and the laser pulse of several μs to hundreds of μs.

Technical problems of the inventive concept are not limited to the technical problems mentioned above, and other technical problems not mentioned will be clearly understood by those skilled in the art from the following description.

A skin care device using a multiple composite laser pulse according to an embodiment of the present disclosure may include a laser generating unit including an energy portion configured to supply energy, a light emitting portion configured to generate light by absorbing the energy supplied from the energy portion, a first mirror and a second mirror configured to form a resonance path in which the light generated from the 1 light emitting portion is amplified, a polarizing portion disposed on an optical resonant path between the first mirror and the second mirror and configured to polarize the light, and a first switch and a second switch configured to convert a polarization component of an incident polarized light; and a control unit configured to control the first switch and the second switch such that the laser generating unit operates in a single laser pulse mode or a multiple laser pulse mode.

In the present embodiment, the control unit may control the first switch and the second switch such that at least one of a multiple laser pulse having a width of a first time or a multiple laser pulse having a width of a second time different from the first time is generated, in the multiple laser pulse mode.

In the present embodiment, the polarization component of the incident polarized light polarized by the polarizing portion may not be converted into another polarization component, when no electrical signal is applied to the first switch or the second switch.

In the present embodiment, the polarization component of the incident polarized light polarized by the polarizing portion may be converted into another polarization component, when an electrical signal is applied to the first switch or the second switch.

In the present embodiment, the laser pulse outputted from the laser generating unit may have a width of a time identical to a time of generating light by the light emitting portion, when no electrical signal is applied to the first switch or the second switch.

In the present embodiment, the laser pulse outputted from the laser generating unit may have a width of a time identical to a time of an electrical signal applied to one of the first switch or the second switch, when an electrical signal is applied to the first switch or the second switch.

In the present embodiment, the laser pulse may not output from the laser generating unit when an electrical signal is applied to one of the first switch and the second switch, and not applied to the other.

In the present embodiment, the control unit may include an energy portion controller configured to control an energy supply of the energy portion, a first switch controller configured to control an operation of the first switch, and a second switch controller configured to control an operation of the second switch.

In the present embodiment, the first switch controller may generate an electrical signal of a predetermined time of several ns to tens of ns, and the second switch controller may generate an electrical signal of a variable time of several μs to hundreds of μs.

A skin care method using a multiple composite laser pulse according to an embodiment of the present disclosure may include generating laser using a laser generating unit including an energy portion for supplying energy, a light emitting portion for generating light by absorbing the energy supplied from the energy portion, a first mirror and a second mirror that form a resonance path in which the light generated from the light emitting portion is amplified, a polarizing portion disposed on an optical resonant path between the first mirror and the second mirror to polarize the light, and a first switch and a second switch for converting a polarization component of an incident polarized light; and controlling the first switch and the second switch such that the laser generating unit operates in a single laser pulse mode or a multiple laser pulse mode.

In the present embodiment, the first switch and the second switch may be controlled such that at least one of a multiple laser pulse having a width of a first time or a multiple laser pulse having a width of a second time different from the first time is generated, in the multiple laser pulse mode.

In the present embodiment, the first switch and the second switch may operate while the energy portion supplies energy of a first period, and the first switch and the second switch may not operate while the energy portion supplies energy of a second period.

In the present embodiment, the first switch and the second switch may operate while the energy portion supplies energy of a first period, and the first switch and the second switch may operate while the energy portion supplies energy of a second period.

In the present embodiment, the first switch and the second switch may not operate while the energy portion supplies energy of a first period, and the first switch and the second switch may operate while the energy portion supplies energy of a second period.

In the present embodiment, the first switch and the second switch may not operate while the energy portion supplies energy of a first period, and the first switch and the second switch may not operate while the energy portion supplies energy of a second period.

DETAILED DESCRIPTION

Figure 1:
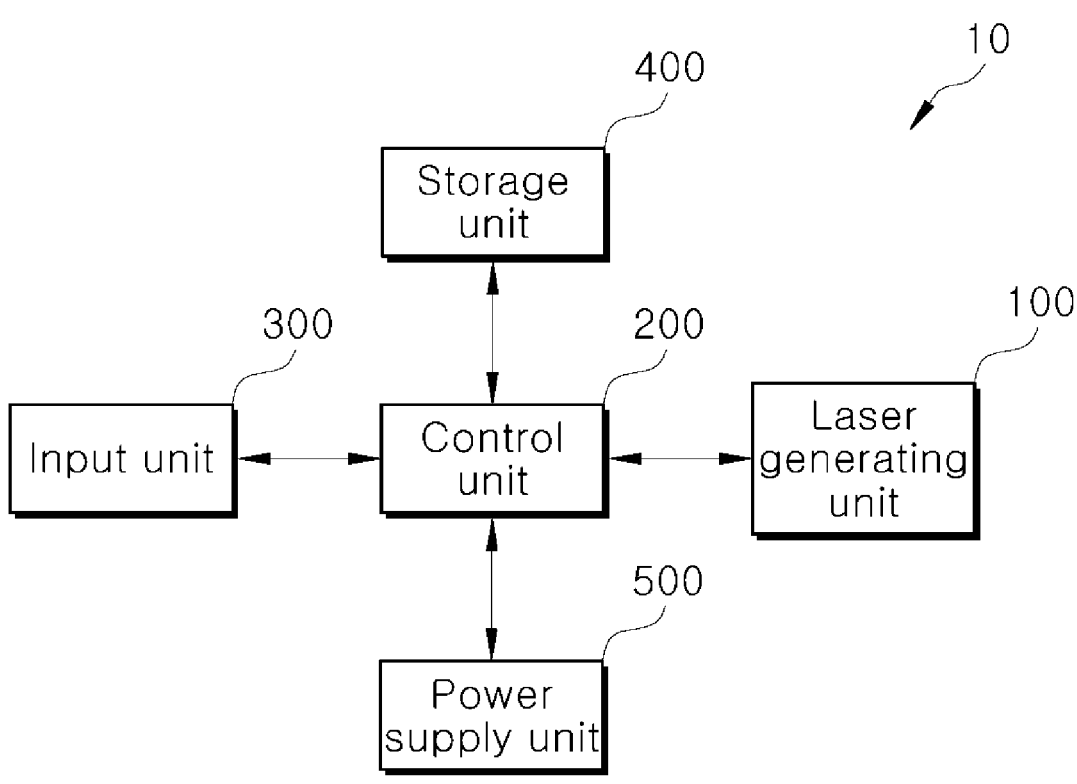
FIG. 1 is a block diagram schematically illustrating a skin care device using a multiple composite laser pulse according to an embodiment of the present disclosure.

Hereinafter, an embodiment of the present disclosure will be described in detail with reference to the accompanying drawings. However, the accompanying drawings are merely illustrated to more easily disclose the contents of the present disclosure, and it will be readily appreciated by those skilled in the art that the scope of the present disclosure is not limited to the scope of the accompanying drawings.

In addition, the terms used herein are intended only to describe a specific embodiment and are not intended to limit the present disclosure. A singular expression includes a plural expression unless the context clearly indicates otherwise.

In the present disclosure, terms such as first, second, and the like are used for the purpose of distinguishing one component from another component, rather than having a limited meaning.

In the present disclosure, terms such as "include" or "have" are intended to specify the existence of features, numbers, steps, actions, components, parts or combinations thereof described in the disclosure, and should be understood not to preclude the existence or addition of one or more other features or numbers, steps, actions, components, parts or combinations thereof.

In the present disclosure, when a part of an area, a component, or the like is on or above another part, it includes not only a case directly on another part, but also a case in which another area, a component, or the like is interposed in the middle.

In the drawings, the sizes of components may be exaggerated or reduced for convenience of description. For example, the size and thickness of the component shown in the drawing are arbitrarily shown for convenience of description, and thus the present disclosure is not necessarily limited to the illustration.

When some embodiment is differently implementable, a specific process order may be performed differently from the order described. For example, two processes described in succession may be performed substantially simultaneously or may be performed in an order opposite to the described order.

In the present disclosure, when regions, components, or the like are connected, it includes not only a case in which the regions, components, or the like are directly connected, but also a case in which the regions, components, or the like are indirectly connected with other regions or components interposed there between.

A skin care device 10 using a multiple composite laser pulse according to an embodiment of the present disclosure may include a laser generating unit 100 and a control unit 200 as shown in FIG. 1 in an exemplary manner. In addition, the skin care device 10 according to the present embodiment may further include an input unit 300, a storage unit 400, and a power supply unit 500.

Figure 2:
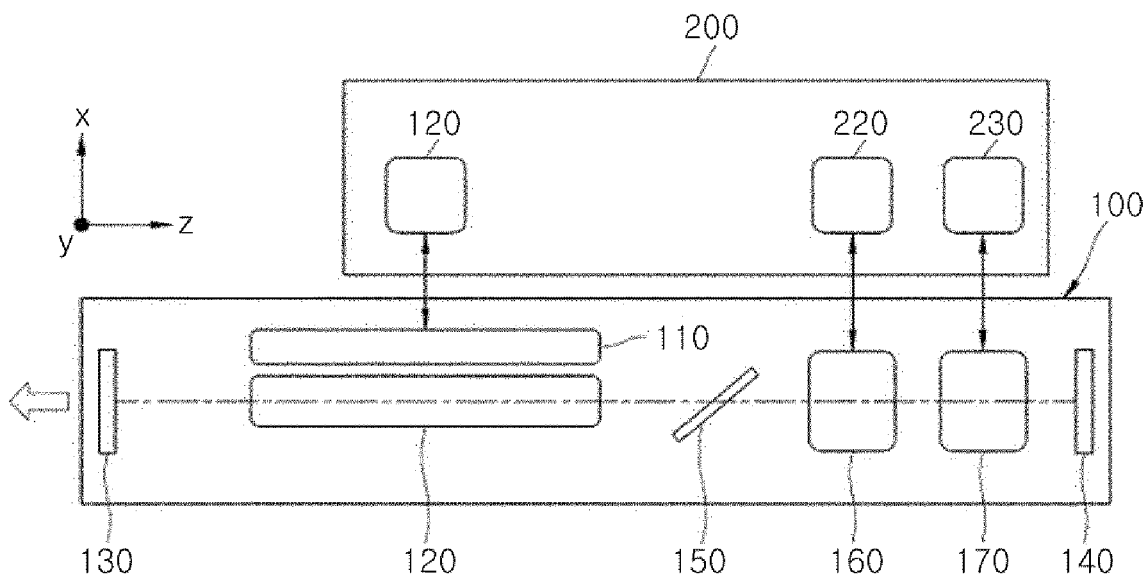
FIG. 2 is a diagram illustrating a laser generating unit and a control unit of a skin care device using a multiple composite laser pulse according to an embodiment of the present disclosure.

The laser generating unit 100 may be a component for generating laser, and as shown in FIG. 2 in an exemplary manner, may include an energy portion 110, a light emitting portion 120, a first mirror 130, a second mirror 140, a polarizing portion 150, a first switch 160, and a second switch 170.

The energy portion 110 may be a component of supplying energy. The energy portion 110 may have various configurations for supplying energy. For example, the energy portion 110 may include a lamp, a laser diode, and a light-emitting diode (LED) to output and supply light energy.

The light emitting portion 120 may be a component for absorbing the energy supplied from the energy portion 110 and generating light. The light emitting portion 120 may have various configurations for absorbing the energy supplied from the energy portion 110 and generating light. For example, the light emitting portion 120 may include a laser medium (laser crystal) such as neodymium-doped yttrium aluminum garnet (Nd:YAG) or erbium-doped yttrium aluminum garnet (Er:YAG) to absorb light energy and generate light. The light emitting portion 120 may generate unpolarized light.

The first mirror 130 and the second mirror 140 may form a resonance path through which the light generated by the light emitting portion 120 is amplified. The first mirror 130 and the second mirror 140 may have various configurations for forming an optical resonance path through which the light generated by the light emitting portion 120 is amplified. For example, the first mirror 130 and the second mirror 140 may be arranged to face each other with the light emitting portion 120 interposed therebetween to form a resonance path of light generated by the light emitting portion 120. One of the first mirror 130 or the second mirror 140 may be a reflective mirror and the other may be an output mirror. For example, the first mirror 130 may be an output mirror, and the second mirror 140 may be a reflective mirror. The first mirror 130, which is the output mirror, may be configured to reflect a part of light and transmit another part of the light. The second mirror 140, which is the reflective mirror, may be configured to reflect all of light.

The polarizing portion 150 may be disposed on the optical resonance path between the first mirror 130 and the second mirror 140 to polarize light. The polarizing portion 150 may have various configurations disposed on the optical resonance path between the first mirror 130 and the second mirror 140 to polarize light. For example, the polarizing portion 150 may be a polarization beam splitter that is disposed on the optical resonance path between the first mirror 130 and the second mirror 140 to separate light to transmit only a predetermined polarization component of incident light. For example, the polarizing portion 150 may be configured to transmit light of P-polarization, which is a polarization in which the electric field of light vibrates in an x-axis direction which is parallel to a plane perpendicular to a traveling direction of light emitted from the light emitting portion 120, and to reflect light of S-polarization, which is a polarization in which the electric field of light vibrates in a y-axis direction which is perpendicular to the plane perpendicular to the traveling direction of light. Accordingly, the polarizing portion 150 may transmit only the light of P-polarization among the light emitted from the light emitting portion 120 and resonate and amplify the light of P-polarization to be outputted as the laser.

The first switch 160 and the second switch 170 may convert the polarization component of an incident polarized light into another polarization component. The first switch 160 and the second switch 170 may have various configurations to convert the polarization component of the incident polarized light into another polarization component. The first switch 160 is also referred to as a first Q-switch and the second switch 170 is also referred to as a second Q-switch.

The first switch 160 and the second switch 170 may be disposed between the polarizing portion 150 and the first mirror 130 or between the polarizing portion 150 and the second mirror 140 in the laser generating unit 100. For example, the first switch 160 may be disposed between the polarizing portion 150 and the second mirror 140, and the second switch 170 may be disposed between the first switch 160 and the second mirror 140. Alternatively, the first switch 160 may be disposed between the polarizing portion 150 and the first mirror 130, and the second switch 170 may be disposed between the first switch 160 and the first mirror 130.

The states of materials that constitute the first switch 160 and the second switch 170 may be changed in response to an application of an electrical signal, and the first switch 160 and the second switch 170 may convert the polarization component of the incident polarized light into another polarization component.

For example, in the case that an electrical signal is not applied to the first switch 160 and the second switch 170, the states of materials that constitute the first switch 160 and the second switch 170 may not be changed, and the first switch 160 and the second switch 170 may operate such that the polarization component of the incident polarized light that has been separated into only a predetermined polarization component by the polarizing portion 150 is not converted into another polarization component. In this case, the laser pulse outputted from the laser generating unit 100 may have the same time as the time of generating light by the light emitting portion 120. For example, the laser pulse may have a time width of several μs to hundreds of μs.

For example, in the case that an electrical signal is applied to the first switch 160 and the second switch 170, the states of materials that constitute the first switch 160 and the second switch 170 may be changed, and the first switch 160 and the second switch 170 may operate such that the polarization component of the incident polarized light that has been separated into only a predetermined polarization component by the polarizing portion 150 is converted into another polarization component.

In the case that the first switch 160 does not operate due to the non-application of an electrical signal and the second switch 170 operates due to the application of an electrical signal, the P-polarized light separated by the polarizing portion 150 among the light emitted by the light emitting portion 120 is converted into a circular polarized light by the second switch 170 although the polarization component is not converted by the first switch 160. Thereafter, the circular polarized light is reflected by the second mirror 140 and then converted into the S-polarized light by the second switch 170. The polarization component of the S-polarized light is not changed by the first switch 160. Accordingly, the S-polarized light may not pass through the polarizing portion 150, which allows only the P-polarized light to pass, and thus may be unable to resonate. Therefore, a laser pulse is not outputted from the laser generating unit 100.

Similarly, in the case that the first switch 160 operates due to the application of an electrical signal and the second switch 170 does not operate due to the non-application of an electrical signal, the P-polarized light separated by the polarizing portion 150 among the light emitted from the light emitting portion 120 is converted into the S-polarized light by the first switch 160 and may not pass through the polarizing portion 150, and thus may be unable to resonate. Therefore, a laser pulse is not outputted from the laser generating unit 100.

In the case that both the first switch 160 and the second switch 170 operate due to the application of an electrical signal, the P-polarized light separated by the polarizing portion 150 among the light emitted from the light emitting portion 120 is converted into the circular polarized light by the first switch 160, and the circular polarized light is converted into the S-polarized light by the second switch 170. Thereafter, the S-polarized light is reflected by the second mirror 140 and then converted back into the circular polarized light by the second switch 170, and the circular polarized light is converted back into the P-polarized light by the first switch 160. Therefore, the P-polarized light passes through the polarizing portion 150, which allows only the P-polarized light to pass, and thus may be able to resonate. In this case, the first switch 160 may operate such that a plurality of times of electrical signals is applied therethrough while an electrical signal is applied to the second switch 170. In this case, the laser pulse outputted from the laser generating unit 100 may generate multiple laser pulses having the same time, e.g., a time width of several ns to tens of ns, as the time of the electrical signal applied to the first switch 160.

The first switch 160 and the second switch 170 may control the time of converting the polarization component of the incident polarized light into another polarization component. For example, the first switch 160 may control the time of an electrical signal applied thereto to several ns to tens of ns, thereby controlling the time of converting the polarization component of the incident polarized light to several ns to tens of ns, and the second switch 170 may control the time of an electrical signal applied thereto to several μs to hundreds of μs, thereby controlling the time of converting the polarization component of the incident polarized light to several μs to hundreds of μs.

The first switch 160 and the second switch 170 may fix or vary the time of converting the polarization component of the incident polarized light into another polarization component. For example, the first switch 160 may fix the time of an electrical signal applied thereto at a specific time of several ns to tens of ns, thereby fixing the time of converting the polarization component of the incident polarized light into another polarization component at several ns to tens of ns, and the second switch 170 may vary the time of an electrical signal applied thereto in a range of several μs to hundreds of μs thereby varying the time of converting the polarization component of the incident polarized light into another polarization component in a range of several μs to hundreds of μs.

The first switch 160 and the second switch 170 may repeat the conversion of the polarization component of the incident polarized light into another polarization component. For example, an electrical signal of several ns to tens of ns may be repeatedly and discontinuously applied to the first switch 160, and thus the first switch 160 may repeatedly and discontinuously convert the polarization component of the incident polarized light into another polarization component for several ns to tens of ns. In addition, an electrical signal of several μs to hundreds of μs may be repeatedly and discontinuously applied to the second switch 170, and thus the second switch 170 may repeatedly and discontinuously convert the polarization component of the incident polarized light into another polarization component for several μs to hundreds of μs.

The control unit 200 may control the first switch 160 and the second switch 170 such that the laser generating unit 100 operates in a single laser pulse mode or a multiple laser pulse mode. The control unit 200 may have various configurations to control the first switch 160 and the second switch 170 such that the laser generating unit 100 operates in a single laser pulse mode or a multiple laser pulse mode.

Figure 3:
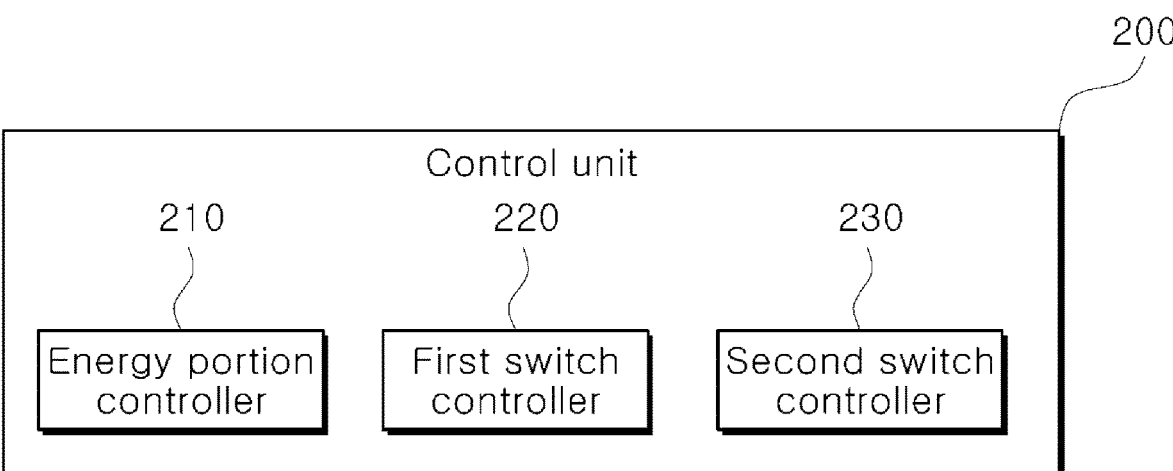
FIG. 3 is a block diagram illustrating a control unit of a skin care device using a multiple composite laser pulse according to an embodiment of the present disclosure.

For example, as shown in FIGS. 2 and 3 in an exemplary manner, the control unit 200 may include an energy portion controller 210, a first switch controller 220, and a second switch controller 230.

The energy portion controller 210 may control an energy supply of the energy portion 110. The energy portion controller 210 may have various configurations to control the energy supply of the energy portion 110. For example, the energy portion controller 210 may control the energy portion 110 to supply a predetermined energy to the light emitting portion 120 for a predetermined time based on input data inputted through the input unit 300 or storage data stored in the storage unit 400. Here, the predetermined energy may be a threshold voltage or greater, e.g., a high voltage, required, to excite the light emitting portion 120 to emit light, and the predetermined time may be a threshold energy or greater, e.g., a high energy to excite the light emitting portion 120 to emit light. The energy portion controller 210 may control the energy portion 110 such that a predetermined energy required to operate the energy portion 110 is supplied from the power supply unit 500.

The first switch controller 220 may control the operation of the first switch 160. The first switch controller 220 may have various configurations to control the operation of the first switch 160. For example, the first switch controller 220 may control the first switch 160 to operate for a predetermined time at a predetermined timing based on input data inputted through the input unit 300 or storage data stored in the storage unit 400. Here, the predetermined timing may be a threshold timing for the first switch 160 operating to convert a polarization component, and the predetermined time may be a threshold time, e.g., a time of several ns, for the first switch 160 operating to convert a polarization component. The first switch controller 220 may supply a predetermined energy, e.g., a high voltage, required to operate the first switch 160. However, the present disclosure is not limited thereto, and the first switch controller 220 may supply a predetermined high voltage autonomously by receiving a signal from the control unit 200. In addition, the first switch controller 220 may control the first switch 160 to operate a plurality of times at predetermined time intervals, e.g., time intervals of 10 μs or more, based on input data inputted through the input unit 300 or storage data stored in the storage unit 400. The first switch controller 220 may also be referred to as a first Q-driver.

The second switch controller 230 may control the operation of the second switch 170. The second switch controller 230 may have various configurations to control the operation of the second switch 170. For example, the second switch controller 230 may control the second switch 170 to operate for a predetermined time at a predetermined timing based on input data inputted through the input unit 300 or storage data stored in the storage unit 400. Here, the predetermined timing may be a threshold timing for the second switch 170 operating to convert a polarization component, and the predetermined time may be a threshold time, e.g., a time of several μs to hundreds of μs, for the second switch 170 operating to convert a polarization component. The second switch controller 230 may supply a predetermined high voltage autonomously by receiving a signal from the control unit 200. However, the present disclosure is not limited thereto, and the second switch controller 230 may control the second switch 170 such that a predetermined high voltage is applied thereto from the power supply unit 500. In addition, the second switch controller 230 may control the second switch 170 to operate a plurality of times at predetermined time intervals, e.g., time intervals of 10 μs or more based on input data inputted through the input unit 300 or storage data stored in the storage unit 400. The second switch controller 230 may also be referred to as a second Q-driver.

The control unit 200 may control the laser generating unit 100 to output a single laser pulse in the single laser pulse mode.

The control unit 200 may control the laser generating unit 100 to generate at least one of a multiple laser pulse having a width of a first time or a multiple laser pulse having a width of a second time different from the first time, in the multiple laser pulse mode.

For example, the control unit 200 may control the energy portion 110, the first switch 160, and the second switch 170 of the laser generating unit 100 by the energy portion controller 210, the first switch controller 220, and the second switch controller 230 to output laser in which a multiple laser pulse of several ns and a multiple laser pulse of several μs to hundreds of μs are combined in various ways from the laser generating unit 100.

Figure 4:
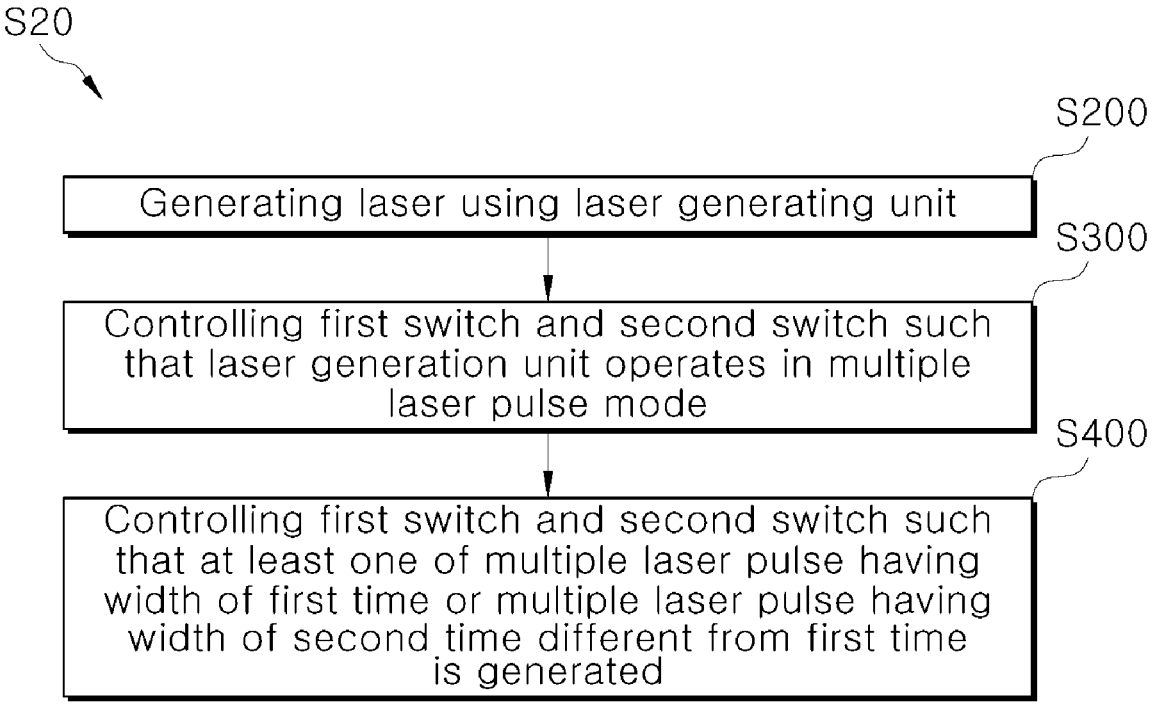
FIG. 4 is a flowchart illustrating a skin care method using a multiple composite laser pulse according to another embodiment of the present disclosure.

The skin care method (S20) using a multiple composite laser pulse according to another embodiment of the present disclosure may include a step (S200) of generating laser using a laser generating unit as exemplified in FIG. 4. Here, the laser generating unit may be the laser generating unit 100 of the skin care device 10 using a multiple composite laser pulse according to an embodiment described above.

The laser generating unit 100 may include the energy portion 110 for supplying energy, the light emitting portion 120 for generating light by absorbing the energy supplied from the energy portion 110, the first mirror 130 and the second mirror 140 that form an optical resonance path in which the light generated from the light emitting portion 120 is amplified, the polarizing portion 150 disposed on the optical resonance path between the first mirror 130 and the second mirror 140 to polarize the light, and the first switch 160 and the second switch 170 for converting the polarization component of the incident polarized light.

The skin care method (S20) using a multiple composite laser pulse according to another embodiment of the present disclosure may include a step (S300) of controlling the first switch 160 and the second switch 170 such that the laser generating unit 100 operates in a single laser pulse mode or a multiple laser pulse mode.

In the multiple laser pulse mode, the first switch 160 and the second switch 170 may be controlled such that at least one of a multiple laser pulse having a width of the first time or a multiple laser pulse having a width of the second time different from the first time is generated (S400).

Such a control may be performed by the control unit 200 of the skin care device 10 using a multiple composite laser pulse according to an embodiment described above.

For example, the control unit 200 may control the energy portion 110, the first switch 160, and the second switch 170 of the laser generating unit 100 by the energy portion controller 210, the first switch controller 220, and the second switch controller 230 to output laser in which a multiple laser pulse of several ns and a multiple laser pulse of several μs to hundreds of μs are combined in various ways from the laser generating unit 100.

1. First Sequence

This is a sequence for which the first switch 160 and the second switch 170 do not operate while the energy portion 110 supplies energy of a first period.

Figure 5:
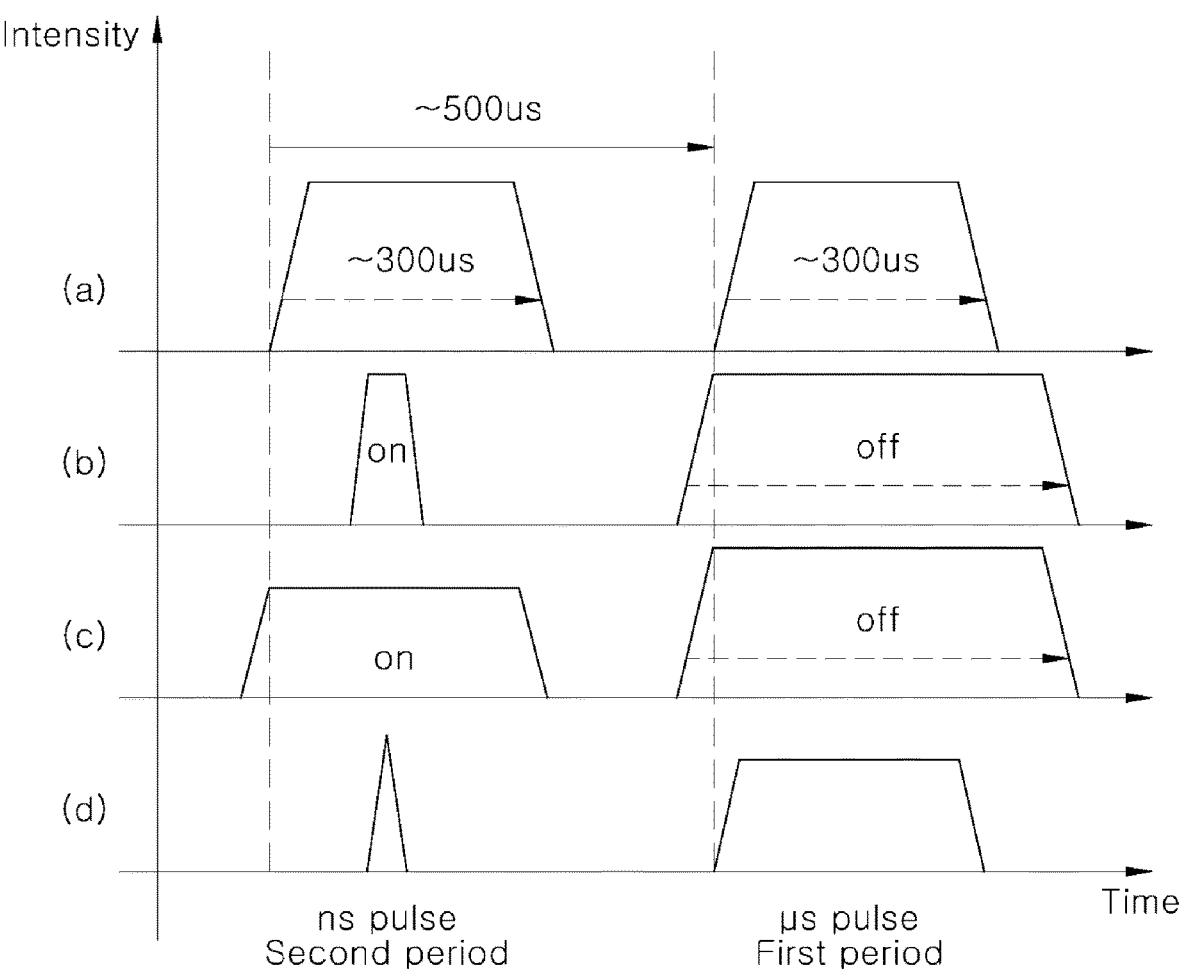
FIG. 5 is a diagram illustrating a generation of a multiple composite laser pulse of a skin care method using a multiple composite laser pulse according to another embodiment of the present disclosure.

As exemplified in (a) of FIG. 5, for the first period, the energy portion controller 210 controls the energy portion 110 to apply an electrical signal having a pulse of 300 μs to the light emitting portion 120 from the power supply unit 500.

The first switch controller 220 controls such that an electrical signal is not applied to the first switch 160, as shown in (b) of FIG. 5.

The second switch controller 230 controls such that an electrical signal is not applied to the second switch 170, as shown in (c) of FIG. 5.

In this case, after an unpolarized light generated by the light emitting portion 120 is polarized to P-polarized light by the polarizing portion 150, the polarization component is not converted by the first switch 160 and the second switch 170, but is amplified in the optical resonance path between the first mirror 130 and the second mirror 140 and output as laser.

The laser outputted as such may be a pulse having a time, e.g., hundreds of μs such as 300 μs, similar to the time of the electrical signal applied to the light emitting portion 120 from the power supply unit 500 by the energy portion 110, as shown in (d) of FIG. 5.

2. Second Sequence

This is a sequence for which the first switch 160 and the second switch 170 operate while the energy portion 110 supplies energy of a second period.

As exemplified in (a) of FIG. 5, the energy portion controller 210 controls the energy portion 110 to repeatedly apply an electrical signal having a pulse of 300 μs to the light emitting portion 120 from the power supply unit 500 for the second period at predetermined time intervals, e,g, time intervals of 200 μs, after the first period is ended.

In the state in which an electrical signal is applied to the second switch 170, the first switch controller 220 controls the first switch 160 such that an electrical signal is applied thereto for a time, e.g., several ns to tens of ns, shorter than the time of the electrical signal applied to the second switch 170, thereby converting the polarization component, as shown in (b) of FIG. 5.

The second switch controller 230 controls the second switch 170 such that an electrical signal is applied thereto for 300 μs or more which is similar to the time of the electrical signal applied to the light emitting portion 120 from the power supply unit 500 by the energy portion 110, thereby converting the polarization component, as shown in (c) of FIG. 5.

In this case, after the P-polarized light among the unpolarized light generated by the light emitting portion 120 is separated by the polarizing portion 150, the P-polarized light undergoes polarization conversion twice by the first switch 160 and the second switch 170 to which an electrical signal has been applied, is then reflected by the second mirror 140, and undergoes polarization conversion again twice by the first switch 160 and the second switch 170 to return to P-polarized light and passes through the polarizing portion 150 to resonate. The laser resonated and outputted as described above may be a pulse having a time, e.g., a time of several ns to several tens of ns, similar to a short time in which an electrical signal is applied to the first switch 160, as shown in (d) of FIG. 5.

3. Combination of First Sequence and Second Sequence

Figure 6:
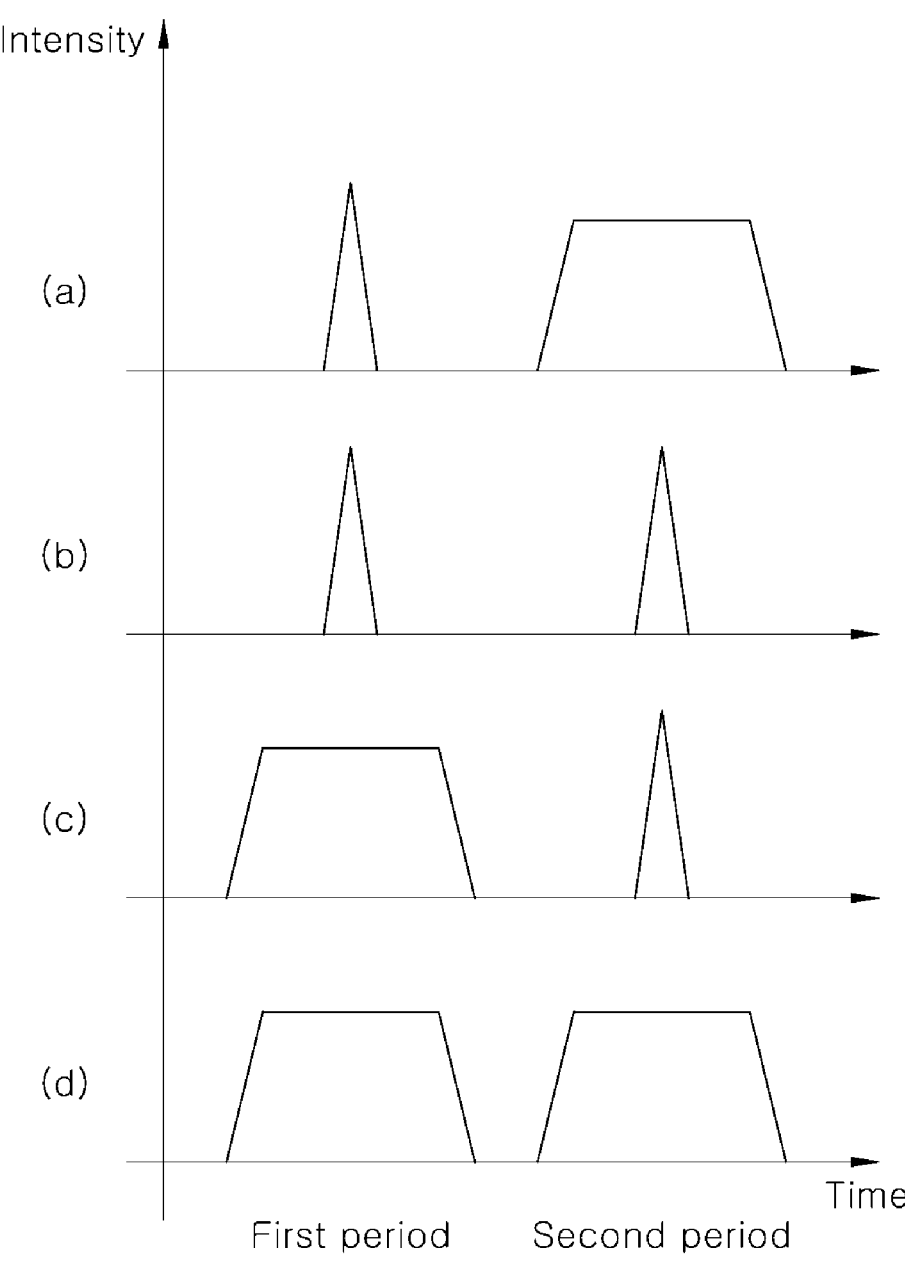
FIG. 6 a diagram illustrating a type of a multiple composite laser pulse of a skin care method using a multiple composite laser pulse according to another embodiment of the present disclosure.

As exemplified in FIG. 6, the first sequence and the second sequence may be combined in various ways to output various types of multiple composite laser pulses.

In the case that the second sequence performed in the first period is combined with the first sequence performed in the second period, the multiple composite laser pulses having a pulse of several ns to tens of ns in the first period and a pulse of hundreds of μs in the second period may be outputted as shown in (a) of FIG. 6. This may be performed by a sequence in which the first switch and the second switch operate while the energy portion supplies the energy of the first period, and the first switch and the second switch do not operate while the energy portion supplies the energy of the second period.

In the case that the second sequence performed in the first period is combined with the second sequence performed in the second period, the multiple composite laser pulses having a pulse of several ns to tens of ns in the first period and a pulse of several ns to tens of ns in the second period may be outputted as shown in (b) of FIG. 6. This may be performed by a sequence in which the first switch and the second switch operate while the energy portion supplies the energy of the first period, and the first switch and the second switch operate while the energy portion supplies the energy of the second period.

In the case that the first sequence performed in the first period is combined with the second sequence performed in the second period, the multiple composite laser pulses having a pulse of hundreds of μs in the first period and a pulse of several ns to tens of ns in the second period may be outputted as shown in (c) of FIG. 6. This may be performed by a sequence in which the first switch and the second switch do not operate while the energy portion supplies the energy of the first period, and the first switch and the second switch operate while the energy portion supplies the energy of the second period.

In the case that the first sequence performed in the first period is combined with the first sequence performed in the second period, the multiple composite laser pulses having a pulse of hundreds of μs output in the first period and a pulse of hundreds of μs in the second period may be outputted as shown in (d) of FIG. 6. This may be performed by a sequence in which the first switch and the second switch do not operate while the energy portion supplies the energy of the first period, and the first switch and the second switch do not operate while the energy portion supplies the energy of the second period.

Figure 7:
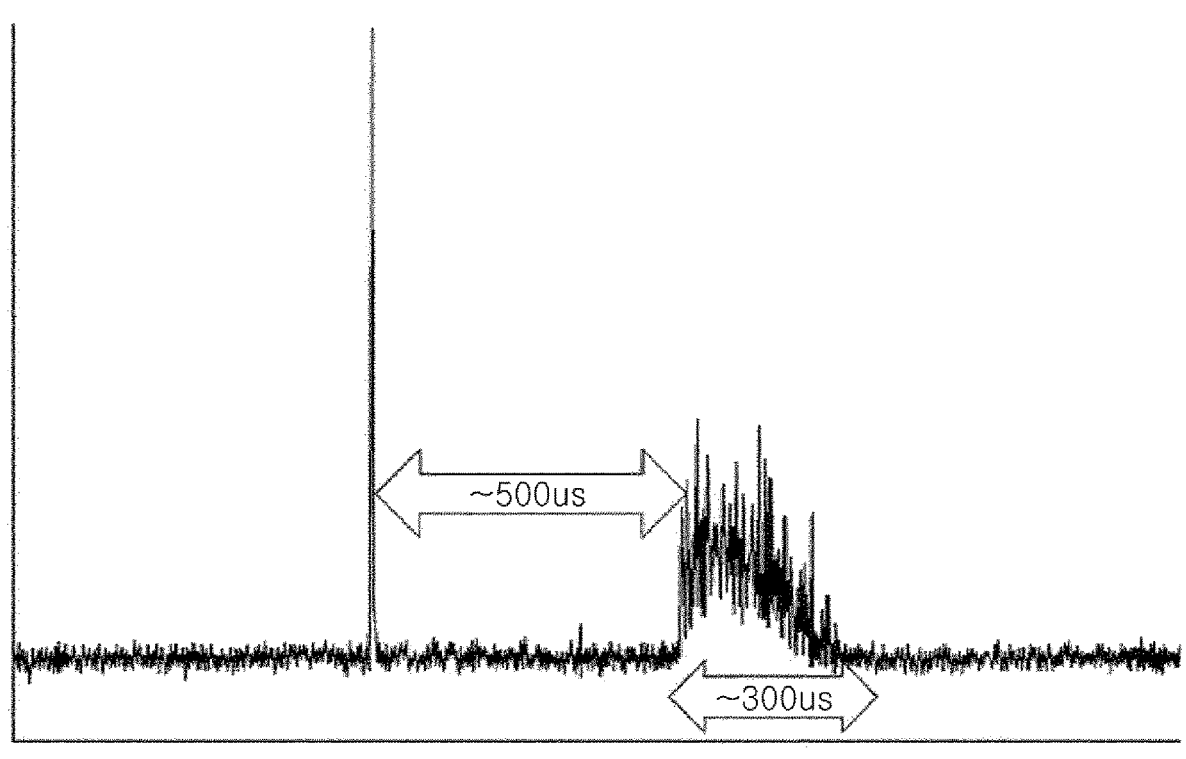
FIG. 7 is a graph illustrating an experimental result of a skin care method using a multiple composite laser pulse according to another embodiment of the present disclosure.

FIG. 7 shows a graph of a multiple composite laser pulse output according to an experimental example for the skin care method using a multiple composite laser pulse according to an embodiment.

Advantageous Effects

The technical effect of the present disclosure may provide a skin care device using a multiple composite laser pulse and a method thereof, which can simultaneously obtain various skin care effects by generating multiple laser pulses of various time widths.

Another technical effect of the present disclosure may provide a skin care device using a multiple composite laser pulse and a method thereof, which can simultaneously obtain the skin care effect, such as removal of pigmented lesions or tattoos, by a laser pulse of several ns to tens of ns, and the skin care effect, such as rejuvenation such as tightening wrinkle improvement, by a laser pulse of several µs to hundreds of µs by repeatedly generating the laser pulse of several ns to tens of ns and the laser pulse of several µs to hundreds of µs.

Still another technical effect of the present disclosure may provide a skin care device using a multiple composite laser pulse and a method thereof, which can simultaneously obtain the skin care effect, such as removal of pigmented lesions or tattoos, by a laser pulse of several ns to tens of ns, and the skin care effect, such as rejuvenation such as tightening wrinkle improvement, by a laser pulse of several µs to hundreds of µs by repeatedly and continuously generating the laser pulse of several ns to tens of ns and the laser pulse of several µs to hundreds of µs at time intervals of about hundreds of µs to hundreds of ms.

Still another technical effect of the present disclosure may provide a skin care device using a multiple composite laser pulse and a method thereof, which can implement multi-laser pulses easily and significantly reduce the time interval between multi-laser pulses by providing at least two electrical switches for repeatedly and continuously generating the laser pulse of several ns to tens of ns and the laser pulse of several µs to hundreds of µs.

Technical effects of the inventive concept are not limited to the technical effects mentioned above, and other technical effects not mentioned will be clearly understood by those skilled in the art from the following description.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative, and accordingly, the present disclosure is not limited to the above description, and may be changed in the scope and equivalence of the accompanying claims.

Particularly, in the embodiments of the present disclosure, the first switch and the second switch are sequentially disposed between the first mirror and the second mirror, but the present disclosure is not limited thereto, and the first switch and the second switch may be disposed in the opposite direction between the first mirror and the second mirror.

INDUSTRIAL APPLICABILITY

An embodiment of the present disclosure may be used for a skin care device and method.

What is claimed is:

1. A skin care device using a multiple composite laser pulse, comprising:
   a laser generating unit including an energy portion configured to supply energy, a light emitting portion configured to generate light by absorbing the energy supplied from the energy portion, a first mirror and a second mirror configured to form a resonance path in which the light generated from the light emitting portion is amplified, a polarizing portion disposed on an optical resonant path between the first mirror and the second mirror and configured to polarize the light, and a first switch and a second switch configured to convert a polarization component of an incident polarized light; and
   a control unit configured to control the energy portion, the first switch, and the second switch to output drive signals that are independently set for each of the first switch and the second switch such that the laser generating unit operates in a single laser pulse mode or a multiple laser pulse mode to output a composite multiple laser pulse,
   wherein the second switch operates to generate a laser pulse having a time width of several microseconds (µs) to several hundreds of microseconds (µs), and the first switch operates one or more times during a period in which the second switch is operating to generate one or more laser pulses having a time width of several nanoseconds (ns) to several tens of nanoseconds (ns).

2. The device of claim 1, wherein the control unit controls the first switch and the second switch such that at least one of a multiple laser pulse having a first time width or a multiple laser pulse having a second time width different from the first time width is generated in the multiple laser pulse mode.

3. The device of claim 1, wherein the polarization component of the incident polarized light polarized by the polarizing portion is not converted into another polarization component, when no electrical signal is applied to the first switch or the second switch.

4. The device of claim 1, wherein the polarization component of the incident polarized light polarized by the polarizing portion is converted into another polarization component, when an electrical signal is applied to the first switch or the second switch.

5. The device of claim 1, wherein the laser pulse outputted from the laser generating unit has a time width that is identical to a time of generating light by the light emitting portion, when no electrical signal is applied to the first switch or the second switch.

6. The device of claim 1, wherein, when an electrical signal is applied to the first switch or the second switch, the laser pulse outputted from the laser generating unit has a time width that is identical to a time width of the electrical signal that is applied.

7. The device of claim 1, wherein the laser pulse is not outputted from the laser generating unit, when an electrical signal is applied to one of the first switch and the second switch, and not applied to the other.

8. The device of claim 1, wherein the laser pulse generated by the second switch ranges from 10 µs to 500 µs in width.

9. A skin care method using a multiple composite laser pulse, comprising:
   generating laser pulse using a laser generating unit including an energy portion for supplying energy, a light emitting portion for generating light by absorbing the energy supplied from the energy portion, a first mirror and a second mirror that form a resonance path in which the light generated from the light emitting portion is amplified, a polarizing portion disposed on an optical resonant path between the first mirror and the second mirror to polarize the light, and a first switch and a second switch for converting a polarization component of an incident polarized light; and
   controlling the energy portion, the first switch, and the second switch to output drive signals that are independently set for each of the first switch and the second switch such that the laser generating unit operates in a single laser pulse mode or a multiple laser pulse mode to output a composite multiple laser pulse,
   wherein the second switch operates to generate a laser pulse having a time width of several microseconds (µs) to several hundreds of microseconds (µs), and the first switch operates one or more times during a period in which the second switch is operating to generate one or more laser pulses having a time width of several nanoseconds (ns) to several tens of nanoseconds (ns).

10. The method of claim 9, wherein the first switch and the second switch are controlled such that at least one of a multiple laser pulse having a first time width or a multiple laser pulse having a second time width different from the first time width is generated in the multiple laser pulse mode.

11. The method of claim 9, wherein the first switch and the second switch operate while the energy portion supplies energy of a first period, and wherein the first switch and the second switch do not operate while the energy portion supplies energy of a second period.

12. The method of claim 9, wherein the first switch and the second switch operate while the energy portion supplies energy of a first period, and wherein the first switch and the second switch operate while the energy portion supplies energy of a second period.

13. The method of claim 9, wherein the first switch and the second switch do not operate while the energy portion supplies energy of a first period, and wherein the first switch and the second switch operate while the energy portion supplies energy of a second period.

14. The method of claim 9, wherein the first switch and the second switch do not operate while the energy portion supplies energy of a first period, and wherein the first switch and the second switch do not operate while the energy portion supplies energy of a second period.

15. The method of claim 9, wherein the laser pulse generated by the second switch ranges from 10 $\mu$s to 500 $\mu$s in width.

\* \* \* \* \*